(12) United States Patent
Sjögren et al.

(10) Patent No.: US 10,813,838 B2
(45) Date of Patent: *Oct. 27, 2020

(54) CONNECTOR FOR FLUID COMMUNICATION

(71) Applicant: BECTON DICKINSON AND COMPANY LTD., Dun Laoghaire (IE)

(72) Inventors: Jesper Sjögren, Nyhamnsläge (SE); Fredrik Ullman, Annelöv (SE)

(73) Assignee: Becton Dickinson and Company Ltd., Dun Laoghaire (IE)

( * ) Notice: Subject to any disclaimer, the term of this patent is extended or adjusted under 35 U.S.C. 154(b) by 78 days.

This patent is subject to a terminal disclaimer.

(21) Appl. No.: 15/639,123

(22) Filed: Jun. 30, 2017

(65) Prior Publication Data

US 2017/0296433 A1 Oct. 19, 2017

Related U.S. Application Data

(63) Continuation of application No. 14/091,603, filed on Nov. 27, 2013, now Pat. No. 9,724,269.

(60) Provisional application No. 61/731,929, filed on Nov. 30, 2012.

(51) Int. Cl.
*A61J 1/20* (2006.01)
*A61M 5/178* (2006.01)

(52) U.S. Cl.
CPC .......... *A61J 1/2096* (2013.01); *A61M 5/1782* (2013.01); *A61J 1/201* (2015.05); *A61J 1/2051* (2015.05); *A61J 1/2055* (2015.05); *A61J 2205/20* (2013.01)

(58) Field of Classification Search
CPC ........ A61J 1/2055; A61J 1/201; A61J 1/2096; A61J 1/2051; A61J 2205/20; A61M 5/1782; B65B 1/04
See application file for complete search history.

(56) References Cited

U.S. PATENT DOCUMENTS

| | | |
|---|---|---|
| 3,047,178 A | 7/1962 | Poitras et al. |
| 3,390,677 A | 7/1968 | Razimbaud |
| 3,826,260 A | 7/1974 | Killinger |

(Continued)

FOREIGN PATENT DOCUMENTS

| | | |
|---|---|---|
| CN | 102196798 A | 9/2011 |
| CN | 102614557 A | 8/2012 |

(Continued)

*Primary Examiner* — Matthew W Jellett
(74) *Attorney, Agent, or Firm* — The Webb Law Firm

(57) ABSTRACT

A fluid connector for selectively establishing fluid communication between a first medical container and a second medical container is provided. The fluid connector includes an adapter configured to removably attach to the first container. The adapter includes an access port and a cap. The connector further includes an outer sleeve connected to the adapter and a tubular body retained at least partially within the outer sleeve. The body has a proximal end connected to the adapter and a distal end connected to the second container. The fluid connector is transitionable from a first position in which the first container and the second container are in fluid isolation to a second position in which the first container and the second container are in fluid communication. At least a portion of the cap of the adapter is retained within the outer sleeve.

19 Claims, 14 Drawing Sheets

(56) References Cited

U.S. PATENT DOCUMENTS

| | | | |
|---|---|---|---|
| 4,564,054 A | 1/1986 | Gustavsson | |
| 4,673,404 A | 6/1987 | Gustavsson | |
| 4,898,209 A * | 2/1990 | Zbed | A61J 1/2089 137/614.04 |
| 5,322,518 A * | 6/1994 | Schneider | A61M 39/24 604/167.03 |
| 5,569,209 A | 10/1996 | Roitman | |
| 5,827,262 A | 10/1998 | Neftel et al. | |
| 6,113,583 A * | 9/2000 | Fowles | A61J 1/10 604/403 |
| 6,149,623 A | 11/2000 | Reynolds | |
| 6,238,372 B1 | 5/2001 | Zinger et al. | |
| 6,280,430 B1 | 8/2001 | Neftel et al. | |
| 6,453,956 B2 * | 9/2002 | Safabash | A61J 1/2096 141/329 |
| 6,746,438 B1 | 6/2004 | Amissolle | |
| 6,852,103 B2 | 2/2005 | Fowles et al. | |
| 7,306,584 B2 | 12/2007 | Wessman et al. | |
| 7,350,535 B2 * | 4/2008 | Liepold | A61M 39/10 137/553 |
| 7,354,427 B2 | 4/2008 | Fangrow | |
| 7,628,772 B2 * | 12/2009 | McConnell | A61J 1/2096 604/181 |
| 7,867,215 B2 | 1/2011 | Akerlund et al. | |
| 7,975,733 B2 | 7/2011 | Horppu et al. | |
| 7,992,597 B2 | 8/2011 | Py et al. | |
| 8,002,130 B2 | 8/2011 | Thilly | |
| 8,096,525 B2 | 1/2012 | Ryan | |
| 8,167,863 B2 | 5/2012 | Yow | |
| 8,196,614 B2 | 6/2012 | Kriheli | |
| 8,211,082 B2 | 7/2012 | Hasegawa et al. | |
| 8,225,826 B2 | 7/2012 | Horppu et al. | |
| 8,225,949 B2 | 7/2012 | Aneas | |
| 8,277,424 B2 | 10/2012 | Pan | |
| 9,114,242 B2 * | 8/2015 | Fangrow | A61M 39/1011 |
| 9,855,192 B2 * | 1/2018 | Kim | A61J 1/2055 |
| 2002/0177819 A1 | 11/2002 | Barker et al. | |
| 2003/0107628 A1 | 6/2003 | Fowles et al. | |
| 2003/0153895 A1 | 8/2003 | Leinsing | |
| 2003/0199846 A1 | 10/2003 | Fowles et al. | |
| 2005/0137566 A1 * | 6/2005 | Fowles | A61J 1/1406 604/412 |
| 2006/0155257 A1 | 7/2006 | Reynolds | |
| 2007/0079894 A1 | 4/2007 | Kraus et al. | |
| 2008/0009789 A1 | 1/2008 | Zinger et al. | |
| 2008/0249479 A1 | 10/2008 | Zinger et al. | |
| 2008/0262466 A1 | 10/2008 | Smith et al. | |
| 2008/0277021 A1 | 11/2008 | Horppu et al. | |
| 2008/0306439 A1 | 12/2008 | Nelson et al. | |
| 2010/0241088 A1 | 9/2010 | Ranalletta et al. | |
| 2011/0004183 A1 | 1/2011 | Carrez et al. | |
| 2011/0022023 A1 | 1/2011 | Weitzel et al. | |
| 2011/0152822 A1 | 6/2011 | Drunk et al. | |
| 2011/0175347 A1 | 7/2011 | Okiyama | |
| 2011/0208128 A1 | 8/2011 | Wu et al. | |
| 2012/0053554 A1 | 3/2012 | Simpson et al. | |
| 2012/0123382 A1 | 5/2012 | Kubo | |
| 2012/0323172 A1 | 12/2012 | Lev et al. | |
| 2013/0076019 A1 | 3/2013 | Takemoto | |
| 2013/0184672 A1 | 7/2013 | Nord et al. | |
| 2014/0150925 A1 | 6/2014 | Sjogren et al. | |
| 2014/0276649 A1 | 9/2014 | Ivosevic et al. | |
| 2014/0311624 A1 | 10/2014 | Eilertsen et al. | |
| 2014/0360623 A1 | 12/2014 | Nielsen et al. | |
| 2015/0082746 A1 | 3/2015 | Ivosevic et al. | |
| 2015/0101706 A1 | 4/2015 | Fukuoka | |
| 2015/0126974 A1 | 5/2015 | Sanders et al. | |

FOREIGN PATENT DOCUMENTS

| | | |
|---|---|---|
| CN | 202408919 U | 9/2012 |
| JP | 6139869 A | 5/1994 |
| JP | 11221782 A | 8/1999 |
| JP | 2005504609 A | 2/2005 |
| JP | 2007295998 A | 11/2007 |
| JP | 2010155100 A | 7/2010 |
| JP | 2010525920 A | 7/2010 |
| JP | 2010538694 A | 12/2010 |
| JP | 201119704 A | 2/2011 |
| JP | 201156009 A | 3/2011 |
| WO | 2008136720 A1 | 11/2008 |

* cited by examiner

CONNECTOR FOR FLUID COMMUNICATION

CROSS-REFERENCE TO RELATED APPLICATION

This application is a continuation of U.S. application Ser. No. 14/091,603, filed Nov. 27, 2013, which claims priority to U.S. Provisional Application Ser. No. 61/731,929, filed Nov. 30, 2012, which is hereby incorporated by reference in its entirety.

BACKGROUND OF THE INVENTION

Field of the Invention

The present invention relates to a connector for enabling fluid transfer between a first fluid container, such as a syringe, and a second fluid container or vial adapter.

Description of Related Art

Fluid connectors, fluid transfer devices, vial adapters, and similar medical apparatuses are commonly used for establishing fluid communication between two medical containers for the purpose of drug reconstitution. Specifically, these devices assist a user to introduce a diluent contained within a first container to a solid, powdered, or lyophilized drug component, contained in a second medical container, such as a medical vial.

Fluid connectors are often used to create a secure connection between a syringe and a second medical container. In this way, the fluid connector serves as an adapter for establishing a connection between the syringe nozzle and the second medical container or an adapter secured to the second medical container. A commonly available fluid connector includes structure for establishing fluid communication between the first container and the second container. Often the fluid flow path through the connector is defined by a needle cannula extending from a first access port, through the connector, to a second access port.

In some configurations, the connector may be transitioned from a first position in which the ports are in fluid isolation to a second position in which fluid communication between the ports is established. For example, in some known fluid connector devices, the connector device includes a telescoping tubular body which can be pressed together to bring the access ports closer together and into contact with the respective ends of the needle. In these devices, a user attaches the medical containers to the ends of the device and then presses on the device body to move the access ports towards one another. As the access ports are brought closer together, the tip of the needle may pierce the ports or medical container closures. In this way, the fluid within the containers is accessible and can be transferred from one container to the other.

In some fluid connector apparatuses, one or both of the access ports includes structure adapted for connection to a corresponding structure of a medical container. However, once the fluid connector has been engaged with the container, there is a risk that the connector may be accidentally or inadvertently disconnected, which could cause fluid contained within the container to leak through the access port, possibly coming into contact with the user. Accidental disconnection of the container and connector presents a serious contamination risk for patients and medical practitioners. Avoiding contamination is especially important when the fluid connector is used to prepare and/or administer a toxic fluid, such as cytostatic agents.

Some medical connectors are further configured to prevent the user from accidentally disconnecting the connector from the container after fluid transfer has been performed. However, these connectors generally do not provide feedback to users about when or if a safe connection has been established between the medical containers. Such connectors also often still allow a user to inadvertently disconnect the connector from the medical container. Furthermore, existing connectors often have a complex external structure which may be confusing for users and may cause users to inadvertently grasp the wrong portion of the connector and to inadvertently disconnect the connector. Examples of conventional medical connectors are shown in U.S. Pat. Nos. 7,306,584; 7,867,215; 7,975,733; and 8,225,826, the entire disclosures of which are each hereby expressly incorporated herein by reference.

SUMMARY OF THE INVENTION

In one embodiment, a fluid connector includes an adapter configured to removably attach to a first container with the adapter having an access port and a cap. An outer sleeve is connected to the adapter and a tubular body is retained at least partially within the outer sleeve. The body has a proximal end connected to the adapter and a distal end connected to a second container where the fluid connector is transitionable from a first position in which the first container and the second container are in fluid isolation, to a second position in which the first container and the second container are in fluid communication. At least a portion of the cap of the adapter is retained within the outer sleeve.

A portion of the cap retained within the outer sleeve may include a latching mechanism configured to engage a corresponding latching structure positioned on an inner sidewall of the outer sleeve. The tubular body may include a needle extending longitudinally through the tubular body from the proximal end to the distal end with the needle defining a lumen. In the first position, the needle may be entirely enclosed within the fluid connector, and in the second position, the needle may extend beyond a distal end of the fluid connector. In the first position, the tubular body may extend beyond a distal end of the outer sleeve, and in the second position, the outer sleeve may cover the tubular body. The outer sleeve may further include an enlarged end portion configured to cover the distal end of the tubular body when the connector is in the second position. The outer sleeve may include a latch for establishing a non-removable engagement with the distal end of the tubular body. The outer sleeve may include a grip portion. The outer sleeve may have a first dominant color and the tubular body may have a second color, with the second color being non-dominant. The tubular body may include a detent, and the outer sleeve may include a notch which, when the connector is in the second position, accepts the detent. The detent may be visible to a user after it is accepted within the notch of the outer sleeve. The outer sleeve may be a first dominant color, the detent may be a second dominant color, and the tubular body may be a non-dominant color. The outer sleeve may include visible lines which are configured to direct a user's attention to the notch.

In a further embodiment, a fluid connector includes an adapter for connecting the connector to a container, an outer sleeve connected to the adapter, and a tubular body retained at least partially within the sleeve. The outer sleeve includes a dominant color and the tubular body comprises a non-dominant color.

The outer sleeve may include a grip portion. The fluid connector may be transitionable from a first position in which a first container and a second container are in fluid isolation, to a second position in which the first container and the second container are in fluid communication. The connector may be configured such that a user transitions the connector from the first position to the second position by grasping the outer sleeve.

In another embodiment, a fluid connector includes an adapter for connecting the connector to a first container, an outer sleeve connected to the adapter, and a tubular body retained at least partially within the sleeve and having a proximal end connected to the adapter and a distal end connected to a second container. The fluid connector is transitionable from a first position in which the first container and the second container are in fluid isolation, to a second position in which the first container and the second container are in fluid communication. The tubular body includes a detent and the outer sleeve defines a notch which, when the connector is in the second position, is configured to accept the detent.

The detent may be visible to a user after it is accepted within the notch of the outer sleeve. The outer sleeve may be a first dominant color, the detent may be a second dominant color, and the tubular body may be a non-dominant color. The outer sleeve may include visible lines which are configured to direct a user's attention to the notch.

BRIEF DESCRIPTION OF THE DRAWINGS

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

DESCRIPTION OF THE INVENTION

Figure 1:
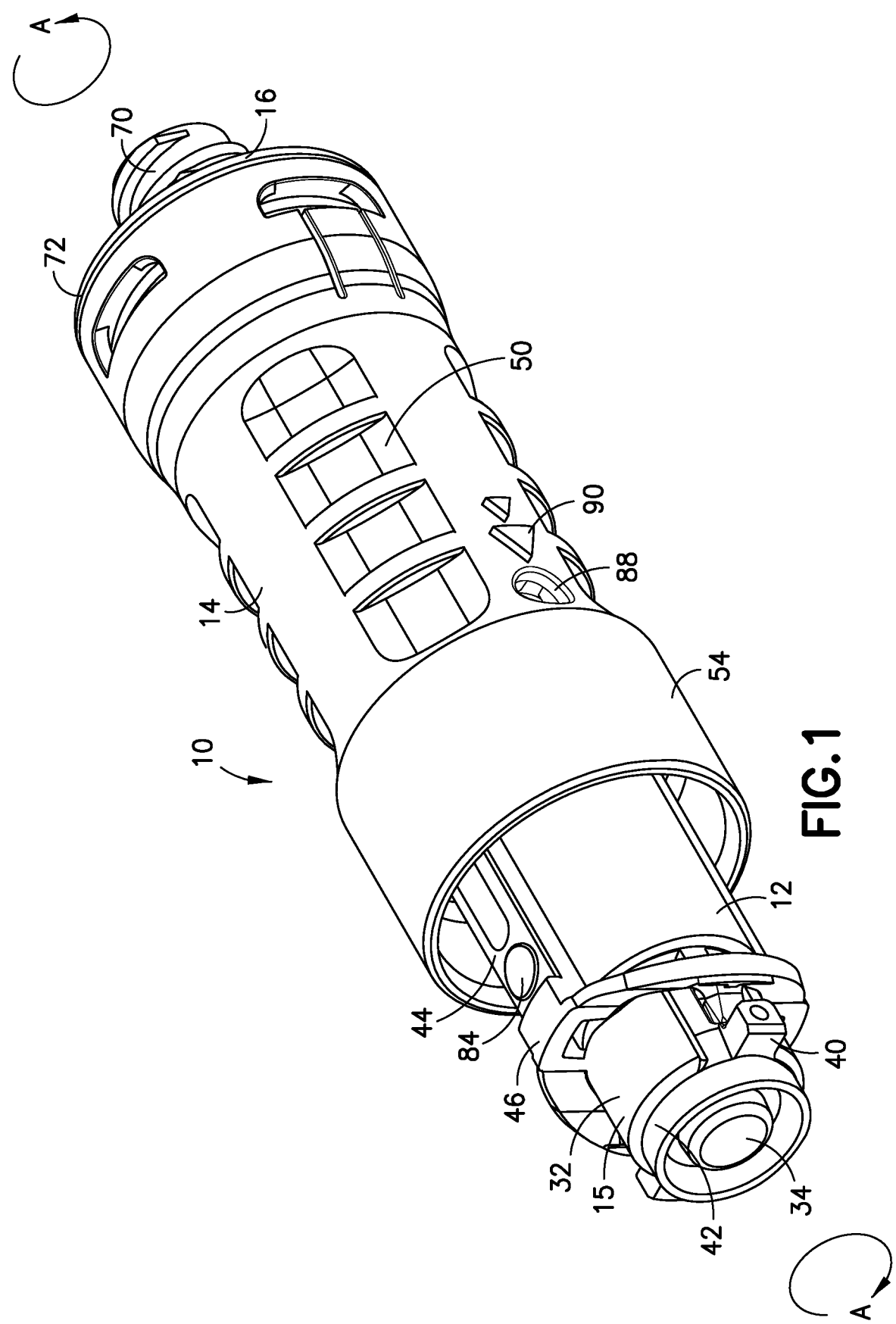
FIG. 1 is a perspective view of a fluid connector configured in the first or storage position in accordance with an embodiment of the present invention.
Figure 2A:
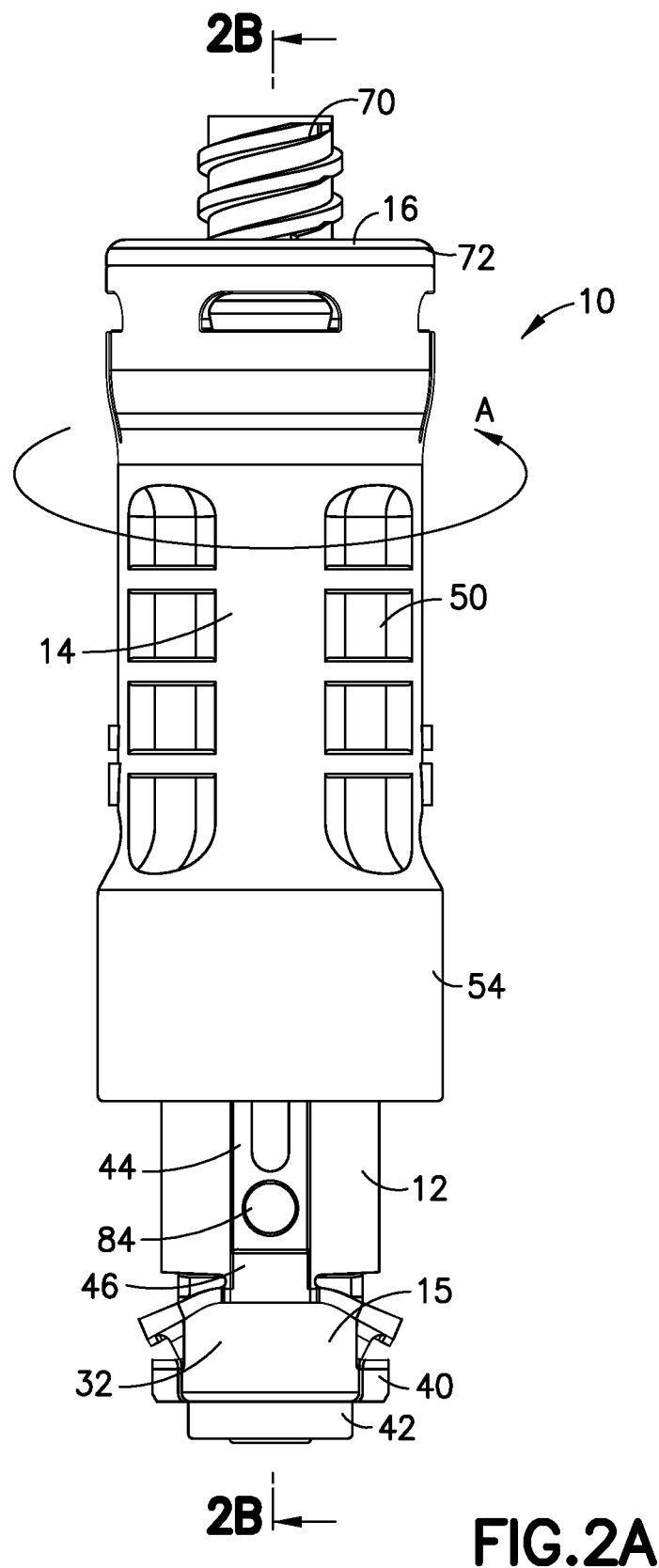
FIG. 2A is a front view of the fluid connector of FIG. 1 in accordance with an embodiment of the present invention.
Figure 2B:
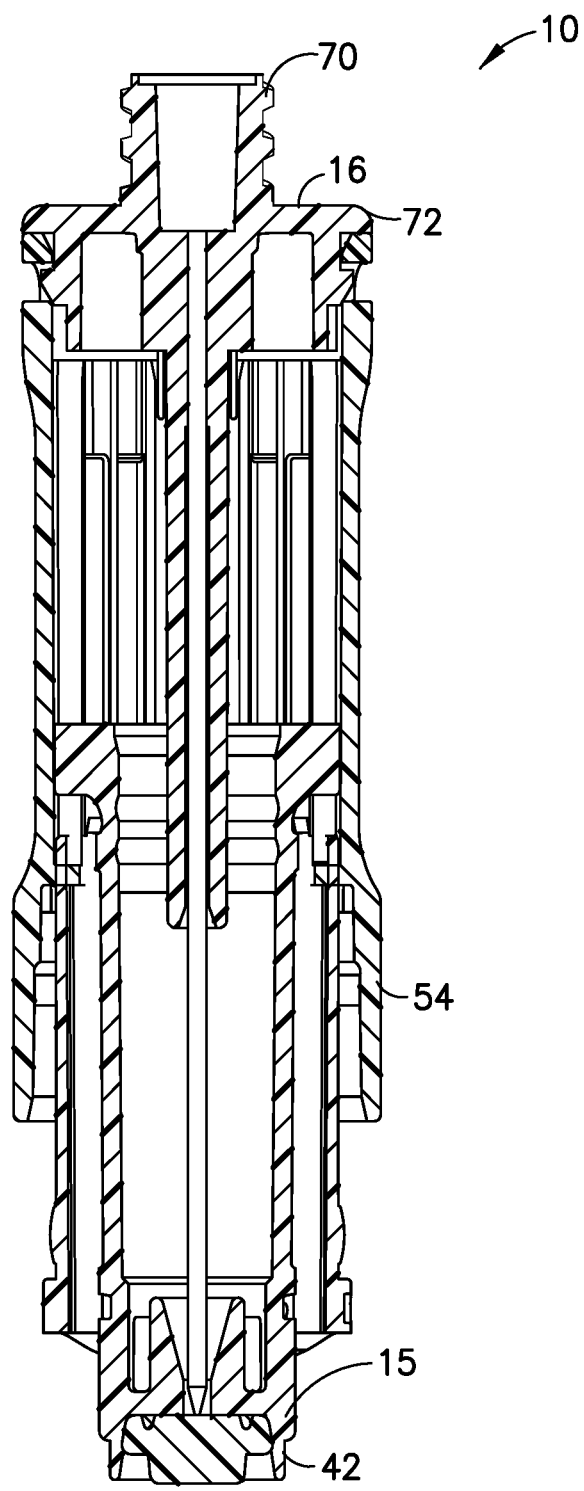
FIG. 2B is a cross-sectional view of the fluid connector of FIG. 1 taken along the line 2B-2B in FIG. 2A.

For the purpose of facilitating understanding of the invention, the accompanying drawings and description illustrate preferred embodiments thereof, from which the invention, various embodiments of its structures, construction and method of operation, and many advantages may be understood and appreciated.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 3:
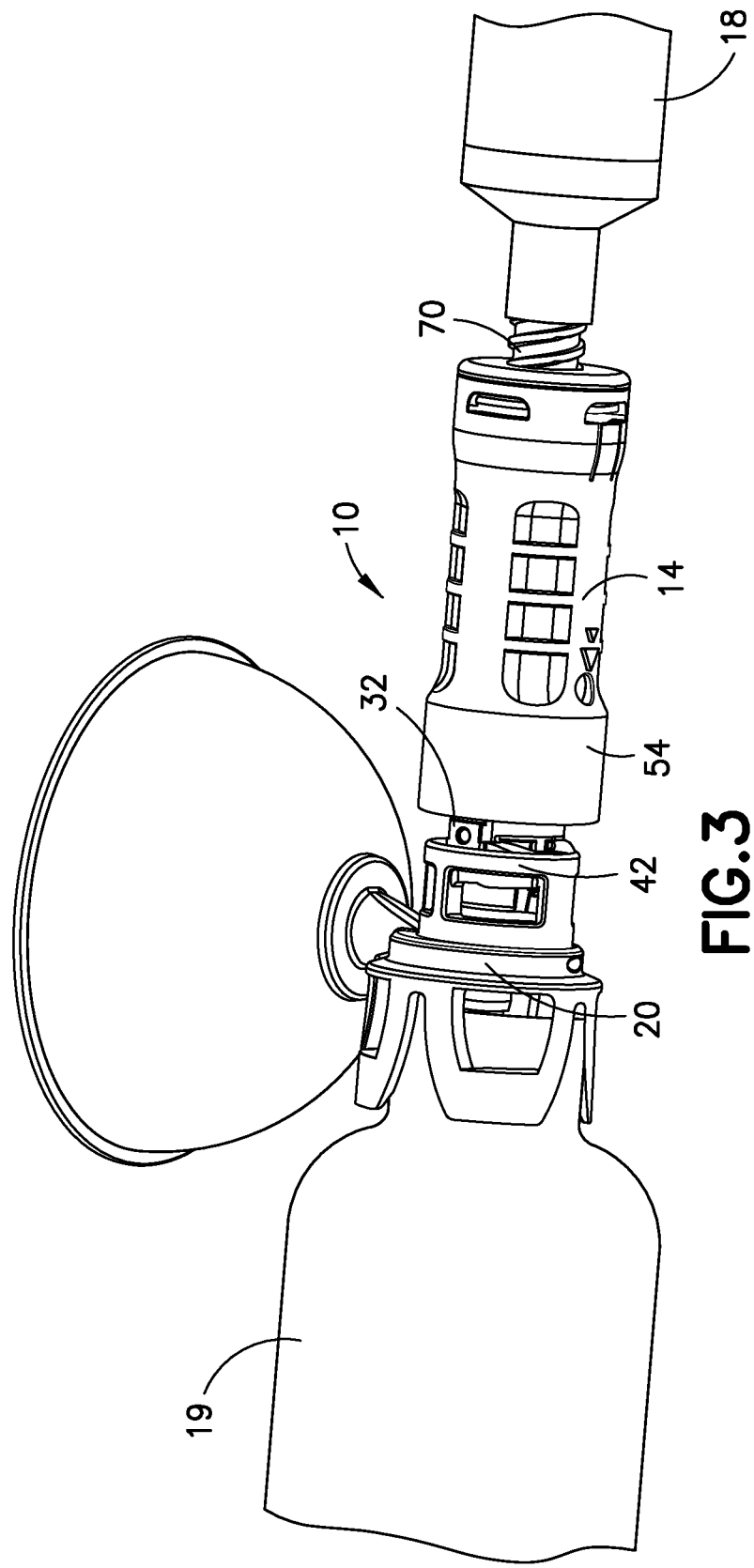
FIG. 3 is a perspective view of the fluid connector of FIG. 1 connected to a syringe on one end and to a vial adapter on the other, in accordance with an embodiment of the present invention.

With reference to FIGS. 1-5, a fluid connector 10 is shown including a tubular body 12, an outer sleeve 14, and an adapter 16. The fluid connector 10 is configured to establish fluid communication between a first medical container 18 and a second medical container 19 or between a medical container 18 and a further apparatus, such as a vial adapter 20. Commonly used medical fluid containers, as is known in the art, include syringes, vials, cartridges, fluid containing bags, medical lines, or similar structures and conduits for holding medical fluids such as drugs, solvents, and diluents. The fluid connector 10 connected between a medical container 18 (e.g., a syringe) and a vial adapter 20 is depicted in FIG. 3. The fluid connector 10 is used to establish fluid communication between the containers so that a user may inject fluid from one container 18 to the other or may draw fluid from one container to the other. The fluid connector 10 also includes structure for locking the device to the first and/or second medical containers and to maintain the connection between the connector and container. Fluid communication between the medical containers is established by moving the outer sleeve 14 from a first position in which a portion of the tubular body 12 extends from the outer sleeve 14, to a second, engaged position in which the outer sleeve 14 encloses the tubular body 12. The fluid connector 10 is shown in the first position in FIG. 4, and in the second position in FIG. 5. The components of the fluid connector 10 are discussed in greater detail below.

Figure 6:
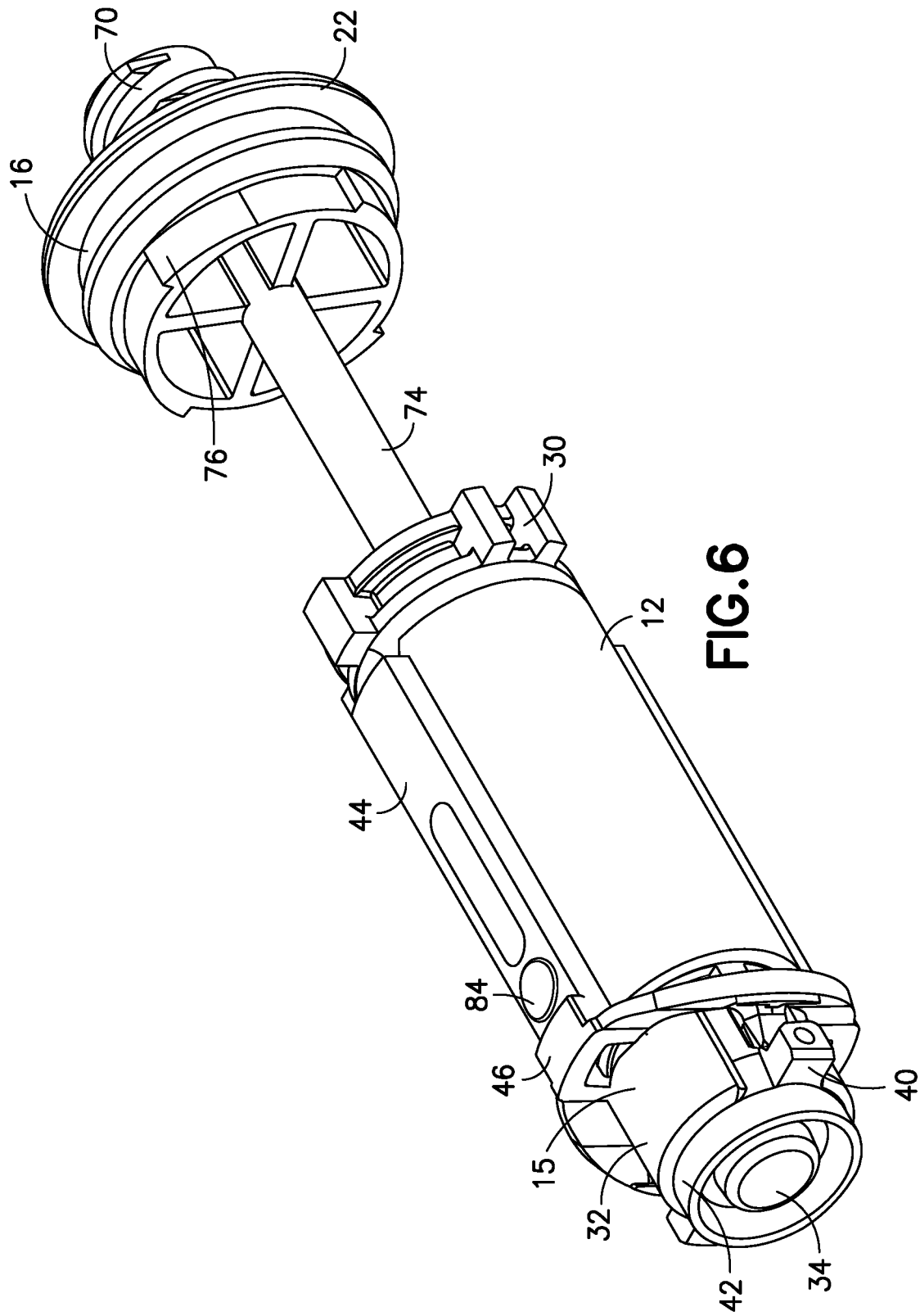
FIG. 6 is a perspective view of the fluid connector of FIG. 1 with the outer sleeve removed to reveal the adapter and tubular body in accordance with an embodiment of the present invention.
Figure 7:
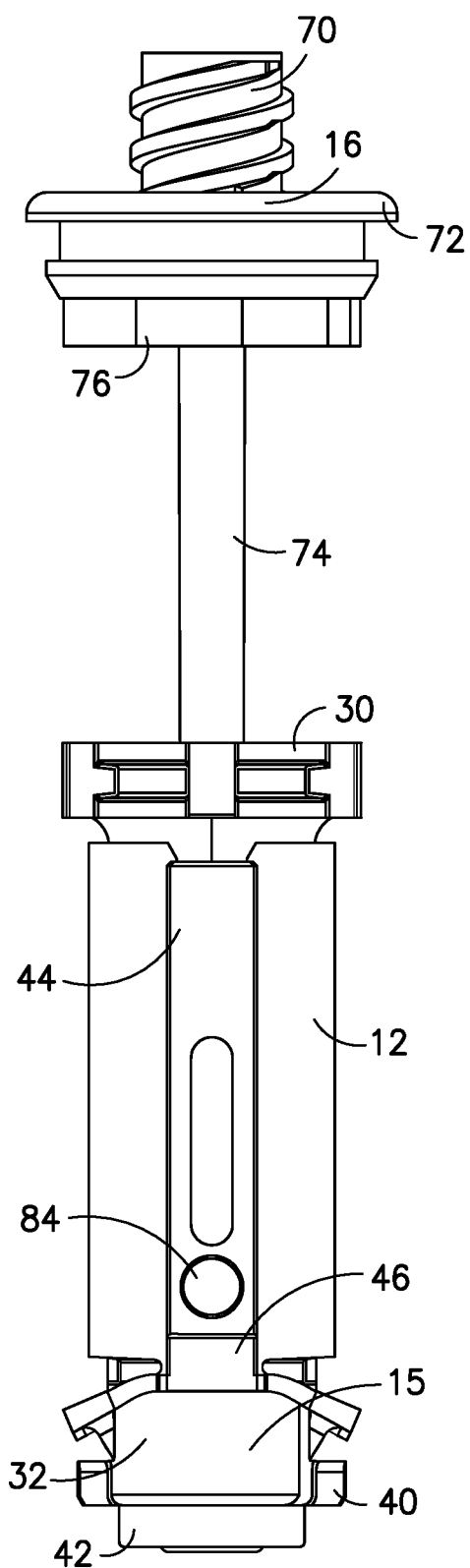
FIG. 7 is a front view of the fluid connector of FIG. 1 with the outer sleeve removed in accordance with an embodiment of the present invention.

With reference to FIGS. 6 and 7, the tubular body 12 has a proximal end 30 located near the adapter 16 and includes an inner sleeve 15 that is received within the tubular body 12. The inner sleeve 15 includes a distal end 32 terminating in a pierceable septum 34 or membrane. The tubular body 12 further includes a needle 36 (shown in FIGS. 11 and 12) extending longitudinally through the inner sleeve 15 and tubular body 12 from the proximal end 30 to the distal end 32. The needle 36 defines a lumen which provides a fluid path through the tubular body 12 and inner sleeve 15. The needle 36 is formed from medical grade metal or other material capable of being sharpened to a tip 38, capable of piercing the septum 34. The needle 36 has a first position in which it is entirely enclosed within the tubular body 12 and a second, exposed position where the needle 36 is forced through the septum 34 and brought into contact with the second medical container 19 or vial adapter 20. The tubular body 12 and inner sleeve 15 are formed from hard plastic or other lightweight but substantially rigid material, although other suitable materials may be utilized. The tubular body 12 and inner sleeve 15 should be sufficiently strong and rigid so that it will not flex or deform during use, specifically when a user pushes on the fluid connector 10 to attach the connector to the medical container 18 or vial adapter 20.

The distal end 32 of the inner sleeve 15 includes a locking structure 40 such as projections, detents, ribs, or threaded connections for connecting the connector 10 to a medical container 19 or vial adapter 20. In certain embodiments, the distal end 32 of the inner sleeve 15 comprises a male connector 42 configured to be received within a female connector of the container 19 or adapter 20. In that case, a user would insert the male connector 42 into the corresponding female connector and twist the tubular body 12 via the outer sleeve 14 to lock it in place. The twisting motion may also be used to release the needle 36 so that it may be moved distally through the tubular body 12. In that way, the tip 38 of the needle 36 is safely retained within the tubular body 12 until the distal end 32 of the tubular body 12 is connected in the female connector. More specifically, the inner sleeve 15 includes structure that cooperates with corresponding structure of the tubular body 12 to selectively allow the inner sleeve 15 to rotate relative to the tubular body 12 which, in turn, allows the needle 36 to be advanced through the septum 34. Thus, rotation of the outer sleeve 14 causes rotation of the inner sleeve 15 to secure the locking structure 40 to the container 19 or adaptor 20 and also allow the needle to extend through the septum 34.

Figure 8:
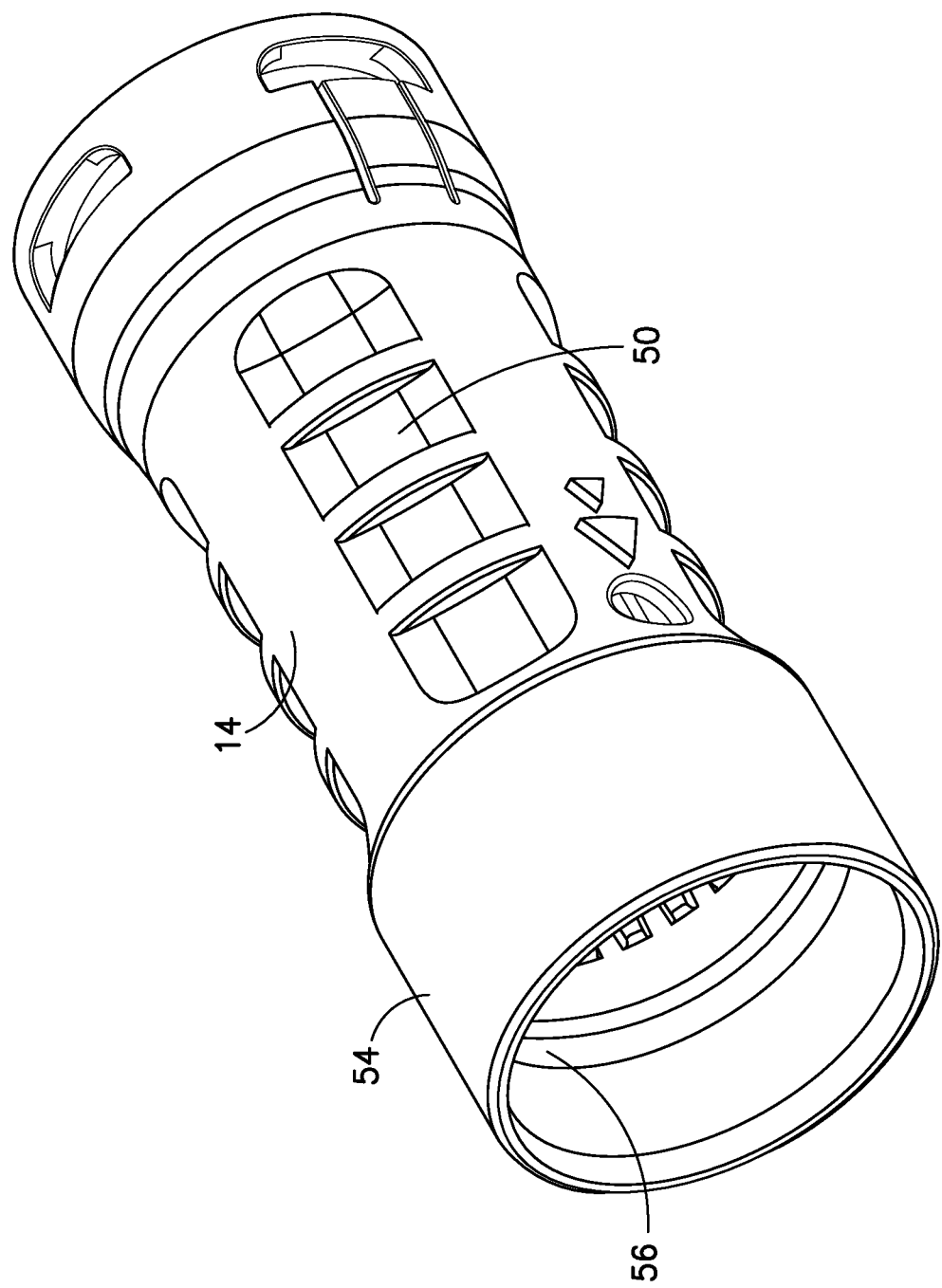
FIG. 8 is a perspective view of the outer sleeve of the fluid connector of FIG. 1 in accordance with an embodiment of the present invention.
Figure 9:
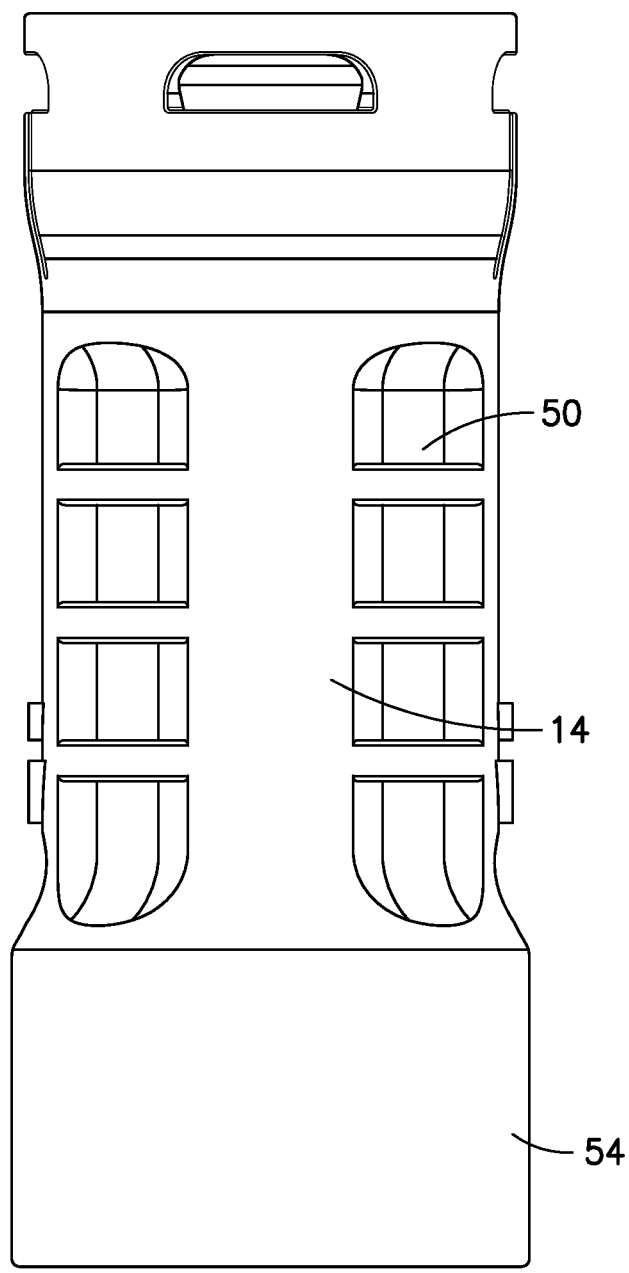
FIG. 9 is a front view of the outer sleeve of FIG. 8 in accordance with an embodiment of the present invention.
Figure 10:
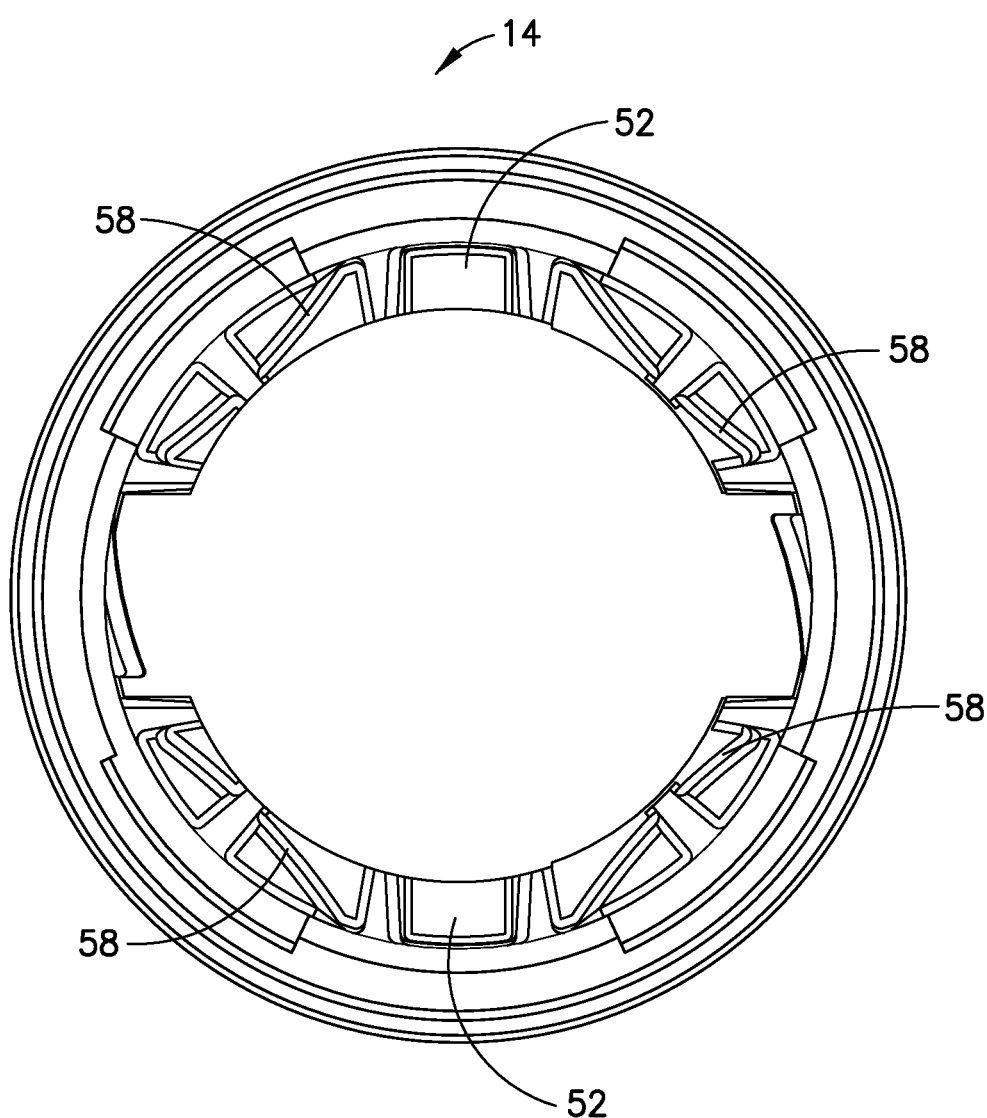
FIG. 10 is a top view of the outer sleeve of FIG. 8 in accordance with an embodiment of the present invention.

With reference to FIGS. 8-10, the outer sleeve 14 of the fluid connector 10 is connected to the adapter 16 and at least partially encloses the tubular body 12. The outer sleeve 14 is configured to be grasped by a user when inserting the connector to the medical container 18 or vial adapter 20. As such, the outer sleeve 14 may have an ergonomic grip 50 to facilitate holding by a user and to improve user comfort.

Figure 4:
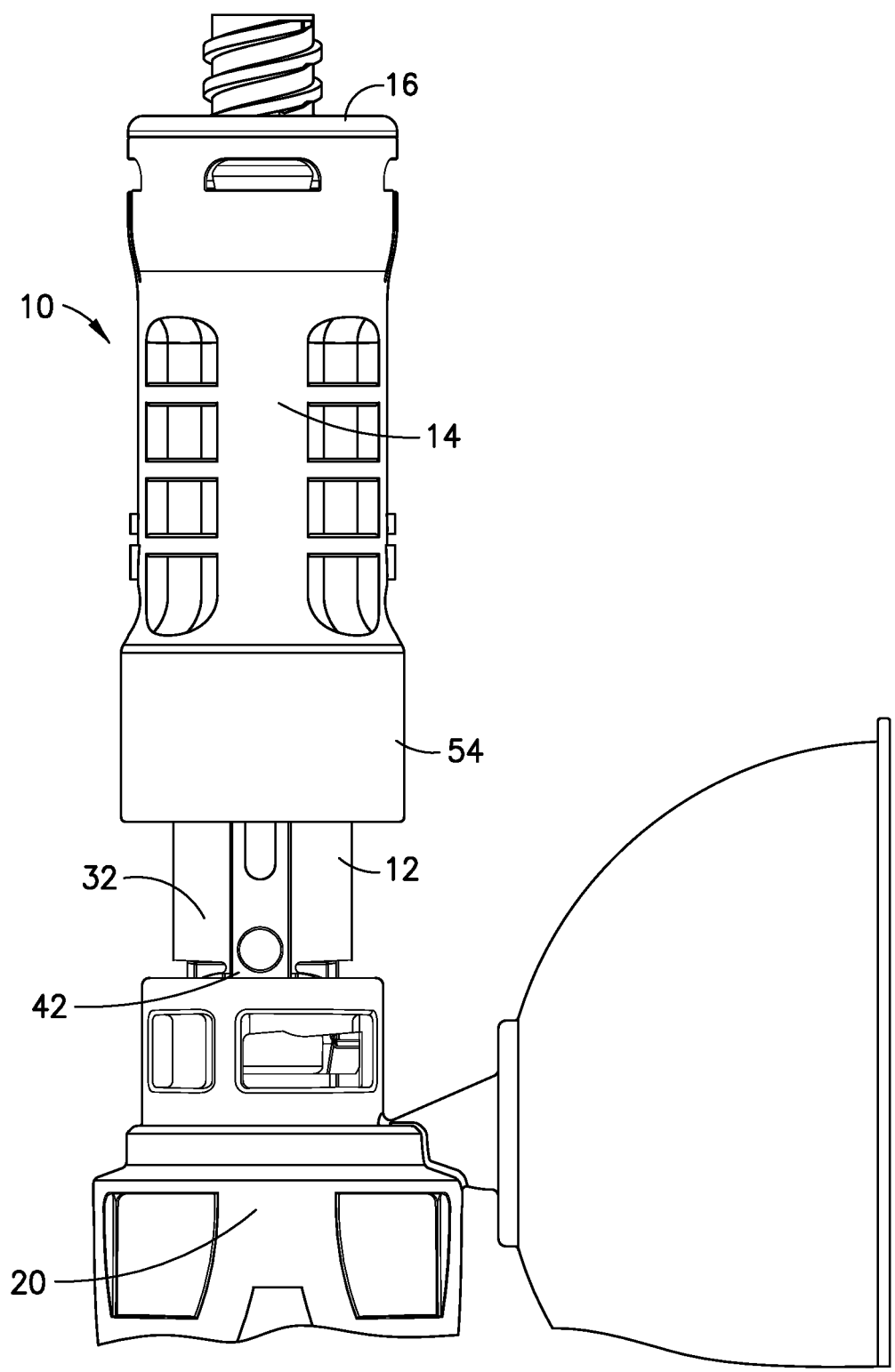
FIG. 4 is a front view of the fluid connector of FIG. 1 connected to a vial adapter, in the first position in accordance with an embodiment of the present invention.
Figure 5:
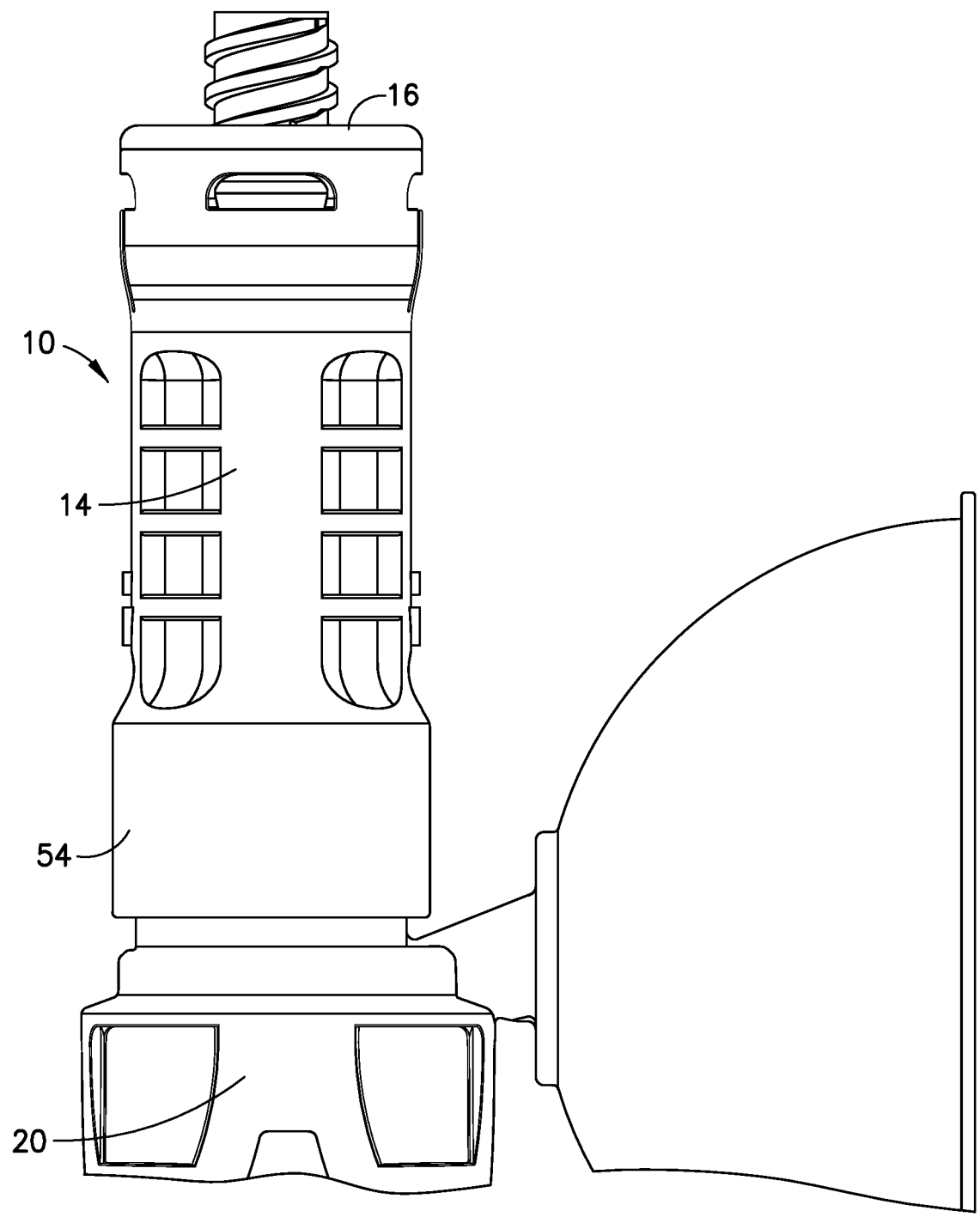
FIG. 5 is a front view of the fluid connector of FIG. 1 in the second position in accordance with an embodiment of the present invention.

As shown in FIGS. 4 and 5, the outer sleeve 14 is configured to slide longitudinally along the tubular body 12 as the connector 10 transitions from the first position to the second position. After securing the connector 10 to the adapter 20 by twisting or rotating the sleeve 14 and locking structure 40, the connector 10 is transitioned between the first position and the second position by pushing or moving the outer sleeve 14 in a longitudinal direction toward the distal end 32, thereby advancing the outer sleeve 14 in the distal direction. The transition of the outer sleeve 14 brings a portion of the adapter 16 in contact with the proximal end 30 of the tubular body 12 and advances the needle 36 through the tubular body 12, as described above, to establish fluid communication between the medical containers 18, 19.

With reference to FIG. 10, the outer sleeve 14 may include one or more longitudinal grooves 52 extending along the inner surface of the sleeve 14. The longitudinal grooves 52 are adapted to receive a longitudinal ridge 44, as shown in FIG. 1, extending along the tubular body 12. Insertion of the ridge 44 within the groove 52 prevents the outer sleeve 14 from rotating relative to the tubular body 12 as the sleeve 14 is pressed downward along the body 12. The outer sleeve 14 may include an enlarged extension 54, as shown in FIGS. 8-9, at the distal end of the sleeve 14. The extension 54 is adapted to cover the tubular body 12 and the distal end 32 of the inner sleeve 15 including the portion of the inner sleeve 15 which engages the container 18 or vial adapter 20.

Figure 11:
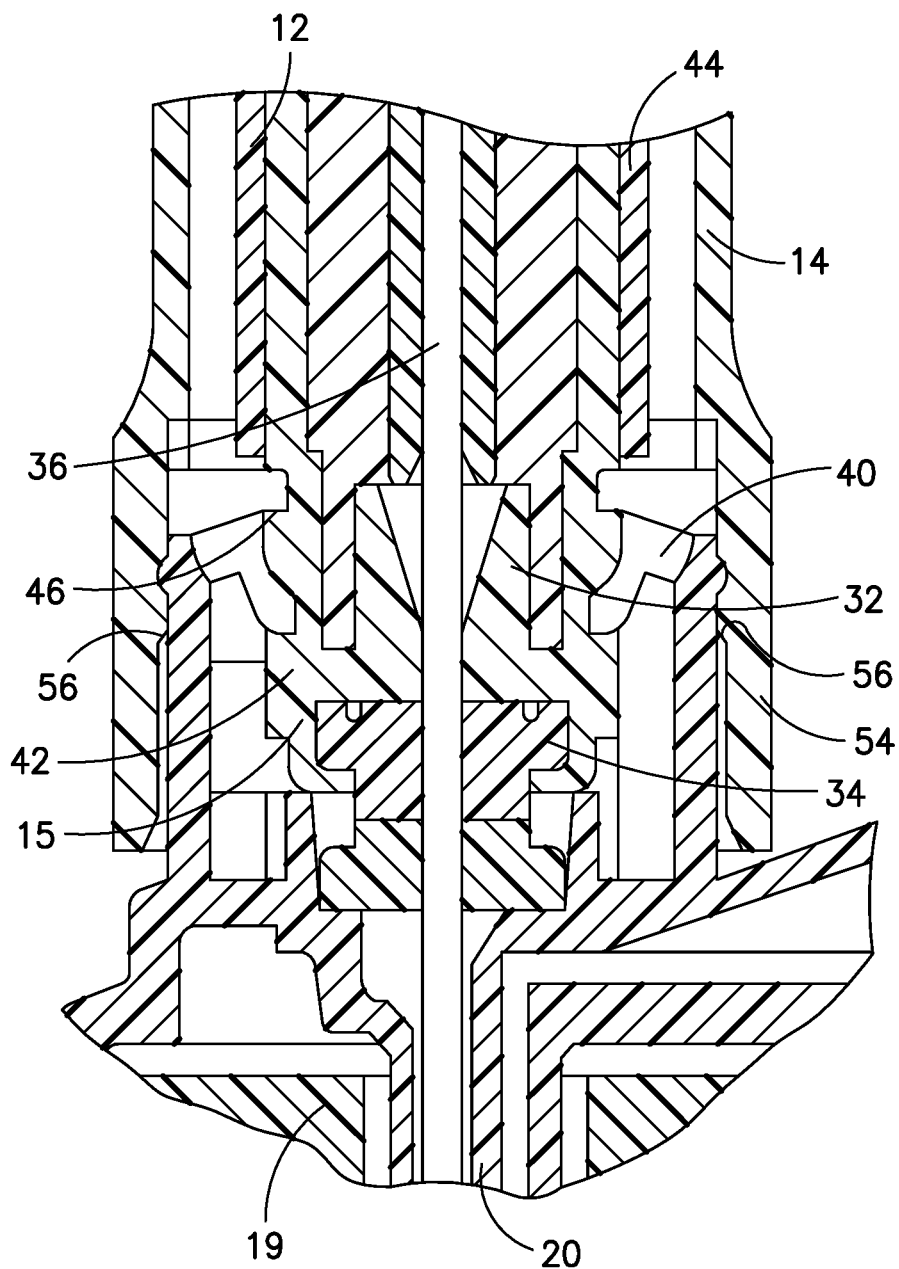
FIG. 11 is a partial cross-sectional view of the fluid connector of FIG. 1, showing the connection between the distal end of the connector and the vial adapter in accordance with an embodiment of the present invention.

With reference to FIG. 11, in a further non-limiting embodiment of the invention, the outer sleeve 14 is configured with a locking mechanism for further securing the outer sleeve 14 in the second position. For example, the outer sleeve 14 may include inward projections 56 located near the distal end of the sleeve 14. The projections 56 may also by positioned on the inner surface of the enlarged extension 54 of the sleeve 14. The projections 56 are configured to grasp and maintain contact with corresponding latches 46 extending radially from the distal end 32 of the inner sleeve 15. When the outer sleeve 14 is transitioned to the second position, the projections 56 engage the latches 46 of the tubular body 12 forming a secure connection therewith. The engagement between the projections 56 and latches 46 maintains the sleeve 14 and tubular member 12 in the second position, thereby reducing the chance of inadvertent disconnection.

Figure 12:
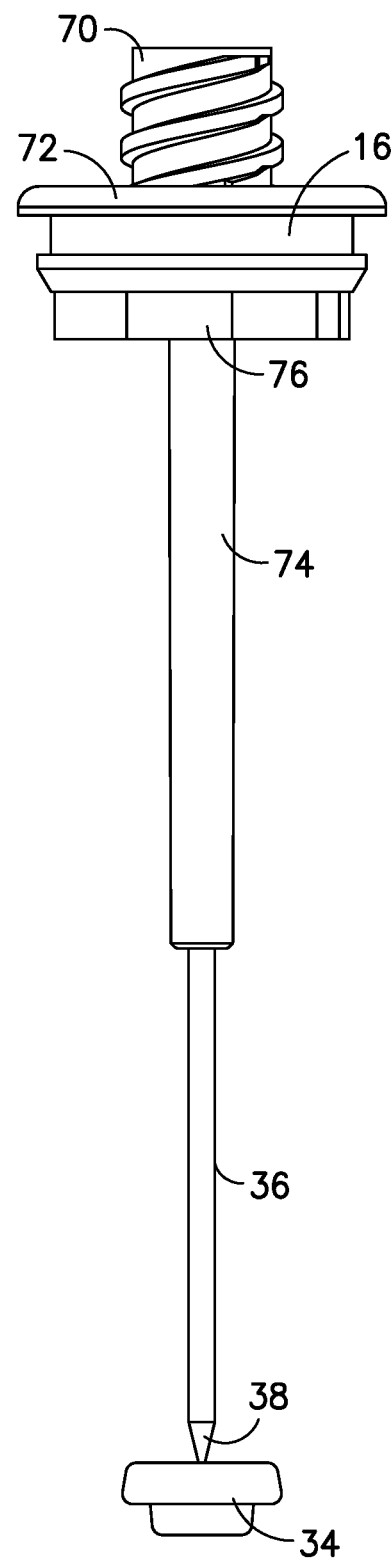
FIG. 12 is a front view of the fluid connector of FIG. 1 with the outer sleeve and tubular body removed to further show the adapter and needle in accordance with an embodiment of the present invention.

With reference now to FIG. 12, the adapter 16 includes a threaded port 70, a cap 72, and a hollow rod 74. The outer sleeve 14 is connected to the adapter 16 at a proximal portion of the sleeve 14. The outer sleeve 14 may include a proximal locking structure 58, as shown in FIG. 10, such as an inwardly projecting rib, latch, or teeth extending from an inner surface of the sleeve 14 to contact and engage the adapter 16. The engagement between the adapter 16 and outer sleeve 14 may prevent rotation of the adapter 16 with respect to the sleeve 14.

With further reference to FIG. 12, the threaded port 70 is configured to connect with a nozzle of a syringe thereby establishing the fluid connection between the medical container 18 and the fluid connector 10. The threaded port 70 extends proximally outward from the cap 72. The cap 72 is generally cylindrical and configured to be inserted in the open proximal end of the outer sleeve 14. The cap 72 may include a protrusion 76, which corresponds to the proximal lock 58 of the outer sleeve 14, for retaining the cap within the outer sleeve. The engagement between the cap 72 and outer sleeve 14 may also prevent rotation of the adapter 16 relative to the outer sleeve 14. The rod 74 extends distally from the threaded port 70 toward the tubular body 12. The rod 74 is rigidly attached to the needle 36 and includes a fluid channel extending through the rod 74 for fluid transfer from the threaded port 70 to the needle 36. As the outer sleeve 14 is transitioned from the first position to the second position, the rod 74 is directed distally and is received within the tubular body 12. Continued distal movement of the rod 74 advances a portion of the needle 36 through the tubular body 12, thereby exposing the tip 38 of the needle 36 through the distal end 32 of the tubular body 12. In the second position, the cap 72 rests against the proximal end 30 of the tubular body 12, and the rod 74 is entirely enclosed within the tubular body 12.

In a preferred and non-limiting embodiment of the invention, the fluid connector 10, especially the outer sleeve 14, is configured to have a minimized diameter. The cap 72 is contained almost entirely within the outer sleeve 14 such that only a proximal most portion of the cap 72 and the threaded port 70 extend beyond the end of the sleeve 14. In this configuration, the cap 72 and at least a portion of the sleeve 14 have substantially the same diameter. An outer sleeve 14 with a reduced diameter can be handled more easily by users. Furthermore, a slimmer outer sleeve 14 is generally more visually pleasing and reduces the apparent complexity of the connector 10 by limiting the components which are visible to a user. In an alternative embodiment, the cap 72 is configured to cover the sleeve 14 such that a portion of the sleeve 14 is enclosed within an interior cavity formed by the cap 72.

In a further non-limiting embodiment of the invention, the connection between the adapter 16 and outer sleeve 14 is a selective rotational engagement which can be transitioned from a freely rotatable configuration in which the adapter 16 can be rotated 360 degrees to a locked or non-rotatable position where rotation of the adapter 16 is prevented. Specifically, the protrusion 76 of the cap 72 forms a ratcheting engagement with the proximal lock 58 of the outer sleeve 14 to allow a syringe or medical container 18 to be connected to the threaded port 70, but discouraging accidental disconnection. Thus, when tightening the medical container 18 to the threaded port 70, rotation between the adapter 16 and the outer sleeve 14 is prevented. When a user attempts to remove the medical container 18 from the threaded port 70, the adapter 16 will rotate relative to the outer sleeve 14 to discourage disconnection.

Figure 13:
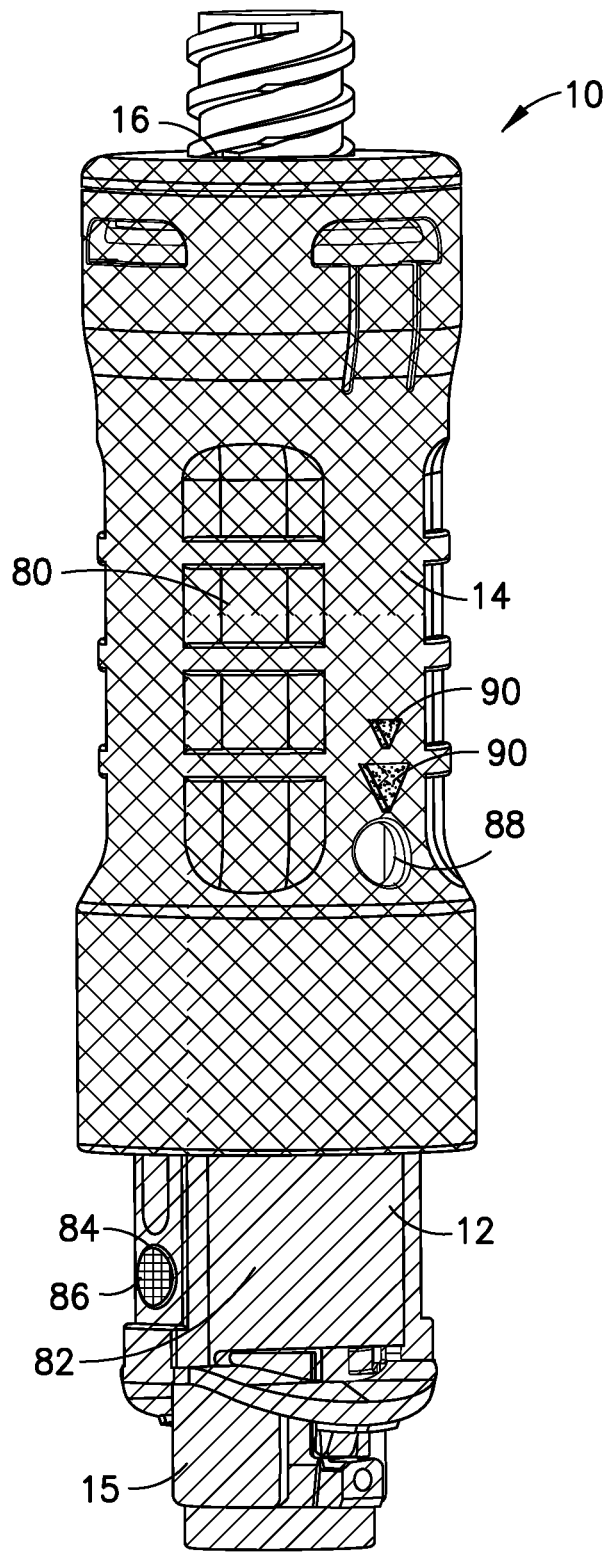
FIG. 13 is a front view of the fluid connector of FIG. 1 showing various indication arrangements in accordance with an embodiment of the present invention.

With reference to FIG. 13, in a further embodiment of the present invention, the connector 10 is provided with a part having a dominant color 80, shown in cross-hatch, and a part having a non-dominant color 82. Users are more likely to grasp and attempt to manipulate portions of a device with the dominant color 80. Therefore, the outer sleeve 14, and specifically the gripping portion 50 of the outer sleeve 14, is provided in the dominant color 80. Dominant colors include red, blue, neon colors, or black, although other suitable dominant colors may be utilized. The tubular body 12, which is not intended to be grasped by the user, is provided in a non-dominant color 82. Non-dominant colors include pastels, neutral colors such as tan, and white. Since the outer sleeve 14 slides distally along the tubular body 12 it is preferable that the user does not attempt to grasp the tubular body 12. Grasping the body 12 would prevent the distal movement of the outer sleeve 14. Using a dominant and non-dominant color scheme encourages the user to hold the correct portion of the fluid connector 10.

While the tubular body 12 is provided mainly with a neutral or non-dominant color 82, the tubular body 12 may further include a visible detent 84, such as a semispherical projection, extending radially from the outer surface of the tubular body 12. The visible detent 84 should be a dominant, highly visible color 86. The visible detent 84 corresponds to and is adapted to be received within a circular notch 88 in the outer sleeve 14. The detent 84 is configured to be received within the notch 88 when the sleeve 14 is in the second position. When the detent 84 aligns with the notch 88, the user is assured that the device has fully transitioned to the second position and that fluid communication through the fluid connector 10 has been established. To further draw a user's attention to the detent 84 and notch 88, the outer sleeve 14 may include visible markings 90 which draw the user's attention to the notch 88. These markings serve to direct the user's attention to the visible detent 84 and encourage the user to check whether the detent 84 and notch 88 are aligned before beginning to inject fluid through the fluid connector 10. The detent 84 may also provide a tactile or haptic feedback to indicate when the connector 10 is in the proper position when in use.

Including features such as the dominant 80 and non-dominant 82 color scheme and visible detent 84 increases user confidence when using the connector 10. The structure and appearance of the device is designed to encourage the user to use the device correctly and to provide visual, tactile, or haptic feedback when a use step has been correctly completed. The visual, tactile, or haptic feedback inspires confidence in a user that subsequent steps will also be correctly completed.

Having described the components of the fluid connector and various exemplary embodiments thereof, a method of using the device will now be described. In use, the fluid connector 10 is initially provided in the first position, as shown, for example, in FIGS. 1 and 2A. The user attaches a syringe to the adapter 16 at the threaded port 70. Specifically, the user places the syringe nozzle about the threaded port 70 and rotates the syringe, thereby engaging the threads of the port 70 with corresponding threads on the inner surface of the syringe nozzle. The user next grasps the fluid connector 10 by the gripping portion 50 located on the outer sleeve 14, and presses the distal end of the device, specifically the distal end 32 of the inner sleeve 15, to a corresponding connector of a fluid container 18 or vial adapter 20. For a male connection, the user pushes the male connector into the corresponding female connector and then rotates the device by grasping the sleeve 14, as shown indicated by line A in FIGS. 1 and 2A, to lock the fluid connector 10 in place.

Once the first medical container 18 (i.e., the syringe) and the second medical container or vial adapter 20 are secured to the fluid connector 10, the device is prepared to be transitioned from the first position to the second position, by distally advancing the outer sleeve 14 relative to the tubular body 12. The user continues to push the outer sleeve 14 in the distal direction until the tubular body 12 is entirely enclosed by the outer sleeve 14 and the outer sleeve cannot advance any further in the distal direction.

Once in the second position, the user is provided with a visual indication that the connector 10 is in the proper position by the detent 84 being received within the notch 88. When the detent 84 and notch 88 are effectively aligned, the user is assured that the device is in the second position, and that fluid communication between the first and second medical containers 18, 19 through the needle 36 has been established. When fluid communication between the first and second containers 18, 19 is established the user is ready to inject fluid from one container 18 to the other 19 or to draw fluid between containers 18, 19. After fluid is transferred between the containers 18, 19, the second container 19 affixed to the distal end of the connector 10 can be removed by moving the sleeve 14 relative to the body 12 to return the connector 10 back to the first position and then grasping and rotating the sleeve 14 and locking structure 40 to disengage the locking structure 40 from the vial adaptor 20.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A fluid connector comprising:
an adapter having an access port, the adapter configured to removably attach to a first container;
an outer sleeve connected to the adapter; and
a tubular body retained at least partially within the outer sleeve, the tubular body having a proximal end connectable to the adapter and a distal end connectable to a second container,
wherein the fluid connector is transitionable from a first position in which the first container and the second container are in fluid isolation to a second position in which the first container and the second container are in fluid communication,
wherein the outer sleeve further comprises an inwardly extending projection for establishing an engagement with the distal end of the tubular body,
wherein the tubular body includes an inner sleeve at least partially received within the tubular body, and
wherein the inner sleeve includes at least one latch that extends radially outward from the inner sleeve to form a secure connection with the inwardly extending projection of the outer sleeve when the fluid connector is in the second position.

2. The fluid connector of claim 1, wherein the outer sleeve comprises an enlarged end portion and wherein the enlarged end portion encloses the distal end of the tubular body when the fluid connector is in the second position.

3. The fluid connector of claim 1, wherein the adapter comprises a cap and wherein at least a portion of the cap retained within the outer sleeve comprises a latching mechanism configured to engage a corresponding latching structure positioned on an inner sidewall of the outer sleeve.

4. The fluid connector of claim 1, wherein the inner sleeve includes a pierceable septum.

5. The fluid connector of claim 4, wherein the tubular body comprises a needle defining a lumen, the needle extending longitudinally through the inner sleeve of the tubular body from the proximal end to the distal end.

6. The fluid connector of claim 5, wherein in the first position, the needle is entirely enclosed within the fluid connector and in the second position the needle pierces the septum and extends beyond a distal end of the fluid connector, and wherein in the first position, the tubular body extends beyond a distal end of the outer sleeve and in the second position the outer sleeve covers the tubular body.

7. The fluid connector of claim 4, wherein the inner sleeve includes a connecting mechanism for connecting the connector to the second container.

8. The fluid connector of claim 4, wherein the inner sleeve is adapted to selectively rotate relative to the tubular body.

9. The fluid connector of claim 1, wherein an inner surface of the outer sleeve defines a longitudinal groove adapted to receive a longitudinal ridge extending at least partially along the tubular body to prevent the tubular body from rotating relative to the outer sleeve.

10. The fluid connector of claim 1, wherein the outer sleeve comprises a gripped portion.

11. The fluid connector of claim 1, wherein the outer sleeve comprises a first color having a first shading and the tubular body comprises a second color having a second shading, in which the first shading is darker than the second shading.

12. The fluid connector of claim 1, wherein the tubular body comprises a detent, and wherein the outer sleeve comprises a notch which, when the fluid connector is in the second position, accepts the detent.

13. The fluid connector of claim 12, wherein the detent is visible to a user after it is accepted within the notch of the outer sleeve.

14. The fluid connector of claim 12, wherein the outer sleeve comprises a first color having a first shading, the detent comprises a second color having a second shading, and the tubular body is a third color having a third shading, in which the first and second shadings are darker than the third shading.

15. The fluid connector of claim 12, wherein the outer sleeve includes visible lines which direct a user's attention to the notch.

16. A fluid connector comprising:
an adapter for connecting the fluid connector to a first container, the adapter comprising an access port and a cap;
an outer sleeve connected to the adapter;
a tubular body retained at least partially within the outer sleeve, the tubular body having a proximal end connectable to the adapter and a distal end connectable to a second container;
an inner sleeve having a structure for cooperating with a corresponding structure of the tubular body to selectively allow the inner sleeve to rotate relative to the tubular body, the inner sleeve comprising at least one locking structure for connecting the fluid connector to the second container; and
a needle at least partially retained within the inner sleeve and transitionable from a first position in which the needle is entirely enclosed within the fluid connector to a second position in which the needle extends beyond a distal end of the fluid connector,
wherein the needle is retained in the first position until the tubular body is connected to the second container,
wherein the outer sleeve includes at least one inwardly extending projection, and
wherein the inner sleeve includes at least one latch that extends radially outward from the inner sleeve to form a secure connection with the inwardly extending projection of the outer sleeve.

17. The fluid connector of claim 16, wherein the inner sleeve comprises a pierceable septum that is pierced when the needle transitions to the second position.

18. The fluid connector of claim 16, wherein the distal end of the tubular body includes a threaded connector adapted to threadably connect with a threaded connector of the second container.

19. The fluid connector of claim 16, wherein the cap comprises a protrusion and wherein the protrusion forms a ratchet engagement with a lock of the outer sleeve allowing the first container to be connected to the access port and preventing disconnection therebetween.

* * * * *